(12) United States Patent
Shi et al.

(10) Patent No.: US 11,875,898 B2
(45) Date of Patent: Jan. 16, 2024

(54) AUTOMATIC CONDITION DIAGNOSIS USING AN ATTENTION-GUIDED FRAMEWORK

(71) Applicant: MERATIVE US L.P., Ann Arbor, MI (US)

(72) Inventors: Luyao Shi, New Haven, CT (US); David James Beymer, San Jose, CA (US); Ehsan Dehghan Marvast, Palo Alto, CA (US); Deepta Rajan, San Jose, CA (US)

(73) Assignee: Merative US L.P., Ann Arbor, MI (US)

( * ) Notice: Subject to any disclaimer, the term of this patent is extended or adjusted under 35 U.S.C. 154(b) by 373 days.

(21) Appl. No.: 17/331,251

(22) Filed: May 26, 2021

(65) Prior Publication Data

US 2022/0384035 A1    Dec. 1, 2022

(51) Int. Cl.
*G06T 7/00* (2017.01)
*G16H 50/20* (2018.01)
(Continued)

(52) U.S. Cl.
CPC ........... *G16H 50/20* (2018.01); *G06F 18/217* (2023.01); *G06T 7/0014* (2013.01); *G16H 30/40* (2018.01);
(Continued)

(58) Field of Classification Search
CPC ...... G16H 50/20; G16H 30/40; G06F 18/217; G06T 7/0014
See application file for complete search history.

(56) References Cited

U.S. PATENT DOCUMENTS 11,710,238 B2   7/2023  Wilson et al.
2018/0082443 A1  3/2018  Risman et al.
(Continued)

FOREIGN PATENT DOCUMENTS

KR         101158041 B1    6/2012

OTHER PUBLICATIONS

Beckman et al. "Venous thromboembolism: a public health concern," American Journal of Preventive Medicine, 2010, 38(4):S495-S501.
(Continued)

*Primary Examiner* — Edward Park
(74) *Attorney, Agent, or Firm* — Michael Best & Friedrich LLP (57) ABSTRACT

Methods and systems for training computer-aided condition detection systems. One method includes receiving a plurality of images for a plurality of patients, some of the images including an annotation associated with a condition; iteratively applying a first deep learning network to each of the images to produce an attention map, a feature map, and an image-level probability of the condition for each of the images; iteratively applying a second deep learning network to each feature map produced by the first network to produce a plurality of outputs; training the first network based on the attention map produced for each image; and training the second network based on the output produced for each of the patients. The second network includes a plurality of convolution layers and a plurality of convolutional long short-term memory (LSTM) layers. Each of the outputs includes a patient-level probability of the condition for one of the patients.

20 Claims, 8 Drawing Sheets
(3 of 8 Drawing Sheet(s) Filed in Color)

(51) Int. Cl.
*G16H 30/40* (2018.01)
*G06F 18/21* (2023.01)
(52) U.S. Cl.
CPC ............. *G06T 2207/20076* (2013.01); *G06T 2207/20081* (2013.01); *G06T 2207/20084* (2013.01); *G06T 2207/30061* (2013.01); *G06T 2207/30101* (2013.01)

(56) References Cited

U.S. PATENT DOCUMENTS

| | | |
|---|---|---|
| 2019/0065817 A1 | 2/2019 | Mesmakhosroshahi et al. |
| 2019/0213482 A1 | 7/2019 | Socher et al. |
| 2020/0272835 A1 | 8/2020 | Cheng et al. |
| 2020/0272888 A1 | 8/2020 | Wang et al. |
| 2022/0058796 A1* | 2/2022 | Vaghefi Rezaei .... A61B 3/0025 |
| 2022/0208355 A1* | 6/2022 | Li .................... G06T 7/0016 |

OTHER PUBLICATIONS

Braman et al. "Disease detection in weakly annotated volumetric medical images using a convolutional LSTM network," arXiv preprint arXiv:1812.01087, 2018, 4 pages.
Carreira et al., Quo vadis, action recognition? a new model and the kinetics dataset. In proceedings of the IEEE Conference on Computer Vision and Pattern Recognition, 2017, pp. 6299-6308.
Gondal et al., "Weakly-supervised localization of diabetic retinopathy lesions in retinal fundus images," In 2017 IEEE International Conference on Image Processing (ICIP), IEEE, 2017, pp. 2069-2073.
Guan et al., "Diagnose like a radiologist: Attention guided convolutional neural network for thorax disease classification," arXiv preprint arXiv:1801.09927, 2018, 10 pages.
He et al. "Deep residual learning for image recognition," In Proceedings of the IEEE Conference on Computer Vision and Pattern Recognition, 2016, pp. 770-778, arXiv preprint arXiv: 1512.03385, 2015, 12 pages.
Huang et al., "Densely connected convolutional networks," In Proceedings of the IEEE conference on computer vision and pattern recognition, 2017, pp. 4700-4708, arXiv preprint arXiv:1608.06993, 2016, 9 pages.
Huang et al., "PENet—A scalable deep-learning model for automated diagnosis of pulmonary embolism using volumetric CT imaging." NPJ Digital Medicine, 2020, 3:61, 9 pages.
Li et al., "Tell me where to look: Guided attention inference network," In Proceedings of the IEEE Conference on Computer Vision and Pattern Recognition, 2018, pp. 9215-9223, arXiv preprint arXiv:1802.10171, 2018, 10 pages.
Liang et al., "Computer aided detection of pulmonary embolism with tobogganing and multiple instance classification in CT pulmonary angiography," Biennial International Conference on Information Processing in Medical Imaging, 2007, pp. 630-641.
Rajan et al., "Pi-PE: A Pipeline for Pulmonary Embolism Detection using Sparsely Annotated 3D Ct Images." arXiv preprint arXiv:1910.02175, 2019, 10 pages.
Selvaraju et al., "Grad-CAM: Visual explanations from deep networks via gradient-based localization," In Proceedings of the IEEE International Conference on Computer Vision, 2017, pp. 618-626, arXiv preprint arXiv: 1610.02391, 2016, 23 pages.
Shamir et al., "Continuous dice coefficient: a method for evaluating probabilistic segmentations," arXiv preprint arXiv: 1906.11031, 2019, 4 pages.
Shi et al., "Convolutional LSTM network: A machine learning approach for precipitation nowcasting," In Advances in Neural Information Processing Systems, 2015, pp. 802-810, arXiv preprint arXiv:1506.04214, 2015, 12 pages.
Shi et al., "Automatic Diagnosis of Pulmonary Embolism Using an Attention-guided Framework: A Large-scale Study," Proc. Third Conference on Medical Imaging with Deep Learning, PMLR 121:743-754, 2020, arXiv preprint arXiv:2006.00074, 2020, 12 pages.
Song et al., "Attend and diagnose: Clinical time series analysis using attention models," 32nd AAAI Conference on Artificial Intelligence, AAAI 2018, arXiv preprint arXiv: 1711.03905, 2017, 8 pages.
Sun et al., "Fast implementation of DeLong's algorithm for comparing the areas under correlated receiver operating characteristic curves," IEEE Signal Processing Letters, 2014, 21(11):1389-1393.
Tajbakhsh et al., "Computer-aided pulmonary embolism detection using a novel vessel-aligned multi-planar image representation and convolutional neural networks," In International Conference on Medical Image Computing and Computer-Assisted Intervention, 2015, pp. 62-69.
Van De Leemput et al., "Stacked bidirectional convolutional LSTMs for deriving 3D non-contrast CT from spa-tiotemporal 4D CT," IEEE transactions on medical imaging, 2019, 9 pages.
Vaswani et al., "Attention is all you need," Advances in neural information processing systems, 2017, arXiv preprint arXiv:1706.03762, 2017, 15 pages.
Yang et al., "A Two-Stage Convolutional Neural Network for Pulmonary Embolism Detection From CTPA Images," in IEEE Access, 2019, 7: 84849-84857.
Yellapragada et al., "Deep learning based detection of acute aortic syndrome in contrast CT images," arXiv preprint arXiv:2004.01648, 2020, 4 pages.
Zhou et al., "Learning deep features for discriminative localization," In Proceedings of the IEEE Conference on Computer Vision and Pattern Recognition, 2016, pp. 2921-2929, arXiv preprint arXiv:1512.04150, 2015, 10 pages.

* cited by examiner

AUTOMATIC CONDITION DIAGNOSIS USING AN ATTENTION-GUIDED FRAMEWORK

FIELD

Embodiments described herein relate to automating diagnosis of a condition, such as pulmonary embolism, using, for example, a deep learning model trained using a two-stage training strategy.

SUMMARY

Pulmonary embolism (PE) is a blockage in a pulmonary artery by a clump of material, most often a blood clot, that is usually formed in the deep veins of patients' legs and travels in the bloodstream up to the lungs. Contrast-enhanced chest CT is commonly used for PE diagnosis. However, manual reading of CT slices by radiologists is laborious, time consuming, and often complicated by false positives caused by various PE look-alike image artifacts, lymph nodes, and vascular bifurcation, among many others. Moreover, the accuracy and efficiency of interpreting such a large image data set is also limited by human's attention span and eye fatigue.

Advancements in deep learning have enabled computer-aided diagnosis (CAD) algorithms to provide accelerated diagnosis that can assist medical professionals in a variety of medical abnormality detection tasks, including diabetic retinopathy, emphysema, and PE. One enduring challenge of training a deep neural network using medical imaging data is the difficulty to collect a sufficiently large annotated data set. Many approaches thus focus on utilizing the more abundant and easily obtainable report-based labeled data to train networks. In the approaches disclosed herein, instead of relying on manually produced pixel-level annotations, patient-level labels are extracted from radiology reports that accompany images.

To help a user understand how and why a network makes predictions, attention maps for a given input image with backpropagation on a convolutional neural network (CNN) can be generated, which reveal which regions on an input image contribute to a prediction. Attention maps can also be used to provide localization information and help build confidence in network predictions. However, supervised by classification loss only, such an end-to-end training often results in attention maps that only cover the most discriminative regions but not necessarily the regions that contain the desired objects (e.g., lesions in medical applications) for classification. For instance, a bias in training data may be encountered where PE lesions incidentally correlate with the same background regions (for example ribs or vertebrae), and, in this case, the training has no incentive to focus attention on the PE. Also, in some cases, automated training may only focus on those background regions where tiny PE lesions are hard to detect. The generalization ability of the trained model is similarly likely to degrade when the testing data has a different correlation.

To address these and other issues, embodiments described herein provide systems and methods for training a deep learning model to detect a medical condition (e.g., PE) based on medical images (e.g., volumetric contrast-enhanced chest computed tomography (CT) scans) using a two-stage training strategy. In a first stage, a two-dimensional (2D) slice-level classification network (also referred to herein as a slice-level classifier) is trained with attention supervision using a relatively small data set of pixel-level annotated slices. In a second stage, a recurrent network is trained to scan through features provided by the slice-level classifier, taking into account the spatial context between the 2D images, and produce a patient-level PE prediction. For this training, a large data set of label-only volumetric images may be used.

Embodiments described herein use attention training (AT), which provides better results on the PE detection task as compared with training using classification loss only. Embodiments described herein can also use a large data set of volumetric images without pixel-level annotations, which can improve classification results even for small objects like PE.

As set forth below with respect to test results associated with various implementations of the systems and methods described herein, embodiments described herein achieve improved results when compared with the state-of-the-art, despite being tested on a much larger and more diverse testing set. Embodiments described herein can also provide localized attention maps that indicate possible PE lesions, which can help radiologist accelerate the diagnostic process. In addition, rather than relying solely on pixel-level annotations or slice-level labels for training, embodiments described herein can take advantage of large data sets of easily obtainable image-label pairs.

In particular, some embodiments described herein provide a method of training a computer-aided condition detection system. The method includes receiving a plurality of medical images for a plurality of patients, a portion of the plurality of medical images including an annotation associated with a condition; iteratively applying a first deep learning network to each of the plurality of medical images to produce an attention map, a feature map, and an image-level probability of the condition for each of the plurality of medical images; iteratively applying a second deep learning network to the feature map produced by the first deep learning network for each of the plurality of medical images to produce a plurality of patient outputs; training the first deep learning network based on the attention map produced by the first deep learning network for each image included in the portion of the plurality of medical images; and training the second deep learning network based on the patient output produced by the second deep learning network for each of the plurality of patients. The second deep learning network includes a plurality of convolution layers and a plurality of convolutional long short-term memory (LSTM) layers. Each of the plurality of patient outputs includes a patient-level probability of the condition for one of the plurality of patients.

Embodiments described herein also provide a system for training a computer-aided condition detection program. The system includes a computing device including an electronic processor. The electronic processor is configured to receive a plurality of medical images for a plurality of patients, a portion of the plurality of medical images including an annotation associated with a condition; iteratively apply a first deep learning network to each of the plurality of medical images to produce an attention map, a feature map, and an image-level probability of the condition for each of the plurality of medical images; iteratively apply a second deep learning network to the feature map produced by the first deep learning network for each of the plurality of medical images to produce a plurality of patient outputs; train the first deep learning network based on the attention map produced by the first deep learning network for each image included in the portion of the plurality of medical images; and train the second deep learning network based on the patient output produced by the second deep learning network for each of the plurality of patients. The second deep learning network includes a plurality of convolution layers and a plurality of convolutional long short-term memory (LSTM) layers. Each of the plurality of patient outputs includes a patient-level probability of the condition for one of the plurality of patients.

Embodiments described herein also provide non-transitory computer-readable medium including instructions that, when executed by an electronic processor, perform a set of functions. The set of functions includes receiving a plurality of medical images for a plurality of patients, a portion of the plurality of medical images including an annotation associated with a condition; iteratively applying a first deep learning network to each of the plurality of medical images to produce an attention map, a feature map, and an image-level probability of the condition for each of the plurality of medical images; iteratively applying a second deep learning network to the feature map produced by the first deep learning network for each of the plurality of medical images to produce a plurality of patient outputs; training the first deep learning network based on the attention map produced by the first deep learning network for each image included in the portion of the plurality of medical images; and training the second deep learning network based on the patient output produced by the second deep learning network for each of the plurality of patients. The second deep learning network includes a plurality of convolution layers and a plurality of convolutional long short-term memory (LSTM) layers. Each of the plurality of patient outputs includes a patient-level probability of the condition for one of the plurality of patients.

Further embodiments described herein provide a method of training a computer-aided condition detection system. The method includes receiving a plurality of medical images for a plurality of patients, a portion of the plurality of medical images including at least one annotation of a condition; iteratively applying a first deep learning network to each of the plurality of medical images to produce a segmentation map, a feature map, and an image-level probability of the condition for each of the plurality of medical images; iteratively applying a second deep learning network to the feature map produced by the first deep learning network for each of the plurality of medical images to produce a plurality of patient outputs; training the first deep learning network based on the segmentation map produced by the first deep learning network for each image included in the portion of the plurality of medical images; and training the second deep learning network based on the patient output produced by the second deep learning network for each of the plurality of patients. The second deep learning network includes a plurality of convolution layers and a plurality of convolutional long short-term memory (LSTM) layers. Each of the plurality of patient outputs includes a patient-level probability of the condition for one of the plurality of patients.

Embodiments described herein also provide a system for training a computer-aided condition detection program. The system includes a computing device including an electronic processor. The electronic processor is configured to receive a plurality of medical images for a plurality of patients, a portion of the plurality of medical images including at least one annotation of a condition; iteratively apply a first deep learning network to each of the plurality of medical images to produce a segmentation map, a feature map, and an image-level probability of the condition for each of the plurality of medical images; iteratively apply a second deep learning network to the feature map produced by the first deep learning network for each of the plurality of medical images to produce a plurality of patient outputs; train the first deep learning network based on the segmentation map produced by the first deep learning network for each image included in the portion of the plurality of medical images; and train the second deep learning network based on the patient output produced by the second deep learning network for each of the plurality of patients. The second deep learning network includes a plurality of convolution layers and a plurality of convolutional long short-term memory (LSTM) layers. Each of the plurality of patient outputs includes a patient-level probability of the condition for one of the plurality of patients.

Embodiments described herein also provide non-transitory computer-readable medium including instructions that, when executed by an electronic processor, perform a set of functions. The set of functions includes receiving a plurality of medical images for a plurality of patients, a portion of the plurality of medical images including at least one annotation of a condition; iteratively applying a first deep learning network to each of the plurality of medical images to produce a segmentation map, a feature map, and an image-level probability of the condition for each of the plurality of medical images; iteratively applying a second deep learning network to the feature map produced by the first deep learning network for each of the plurality of medical images to produce a plurality of patient outputs; training the first deep learning network based on the segmentation map produced by the first deep learning network for each image included in the portion of the plurality of medical images; and training the second deep learning network based on the patient output produced by the second deep learning network for each of the plurality of patients. The second deep learning network includes a plurality of convolution layers and a plurality of convolutional long short-term memory (LSTM) layers. Each of the plurality of patient outputs includes a patient-level probability of the condition for one of the plurality of patients.

Further embodiments described herein provide a method of detecting a condition using a computer-aided condition detection system. The method includes receiving, at the computer-aided condition detection system, a three-dimensional (3-D) medical image for a patient, the 3-D image including a plurality of two-dimensional (2-D) medical images for the patient; iteratively applying a first deep learning network to each of the plurality of 2-D medical images to produce a feature map, the first deep learning network trained using a training set of 2-D images including annotations associated with the condition to minimize classification loss and at least one selected from a group consisting of attention loss and segmentation loss; iteratively applying a second deep learning network to the feature map produced by the first deep learning network for each of the plurality of 2-D medical images to produce a plurality of outputs, the second deep learning network trained using a training set of 3-D images associated with labels indicating presence of the condition; pooling the plurality of outputs to generate a patient-level probability of the patient having the condition; and outputting the patient-level probability. The second deep learning network including a plurality of convolution layers and a plurality of convolutional long short-term memory (LSTM) layers.

Embodiments described herein also provide a system for detecting a condition using a computer-aided condition detection system. The system includes a computing device including an electronic processor. The electronic processor is configured to receive a three-dimensional (3-D) medical image for a patient, the 3-D image including a plurality of two-dimensional (2-D) medical images for the patient; iteratively apply a first deep learning network to each of the plurality of 2-D medical images to produce a feature map, the first deep learning network trained using a training set of 2-D images including annotations associated with the condition to minimize classification loss and at least one selected from a group consisting of attention loss and segmentation loss; iteratively apply a second deep learning network to the feature map produced by the first deep learning network for each of the plurality of 2-D medical images to produce a plurality of outputs, the second deep learning network trained using a training set of 3-D images associated with labels indicating presence of the condition; pool the plurality of outputs to generate a patient-level probability of the patient having the condition; and output the patient-level probability. The second deep learning network including a plurality of convolution layers and a plurality of convolutional long short-term memory (LSTM) layers.

Embodiments described herein also provide non-transitory computer-readable medium including instructions that, when executed by an electronic processor, perform a set of functions. The set of functions includes receiving, at the computer-aided condition detection system, a three-dimensional (3-D) medical image for a patient, the 3-D image including a plurality of two-dimensional (2-D) medical images for the patient; iteratively applying a first deep learning network to each of the plurality of 2-D medical images to produce a feature map, the first deep learning network trained using a training set of 2-D images including annotations associated with the condition to minimize classification loss and at least one selected from a group consisting of attention loss and segmentation loss; iteratively applying a second deep learning network to the feature map produced by the first deep learning network for each of the plurality of 2-D medical images to produce a plurality of outputs, the second deep learning network trained using a training set of 3-D images associated with labels indicating presence of the condition; pooling the plurality of outputs to generate a patient-level probability of the patient having the condition; and outputting the patient-level probability. The second deep learning network including a plurality of convolution layers and a plurality of convolutional long short-term memory (LSTM) layers.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Before embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software-based devices, as well as a plurality of different structural components may be utilized to implement the invention. In addition, embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (for example, stored on non-transitory computer-readable medium) executable by one or more processors. As such, it should be noted that a plurality of hardware and software-based devices, as well as a plurality of different structural components, may be utilized to implement the invention. For example, "computing device," "server," and other electronic devices, as described in the specification, may include one or more electronic processors, one or more memory modules including non-transitory computer-readable medium, one or more input/output interfaces, and various connections (for example, a system bus) connecting the components.

Figure 1:
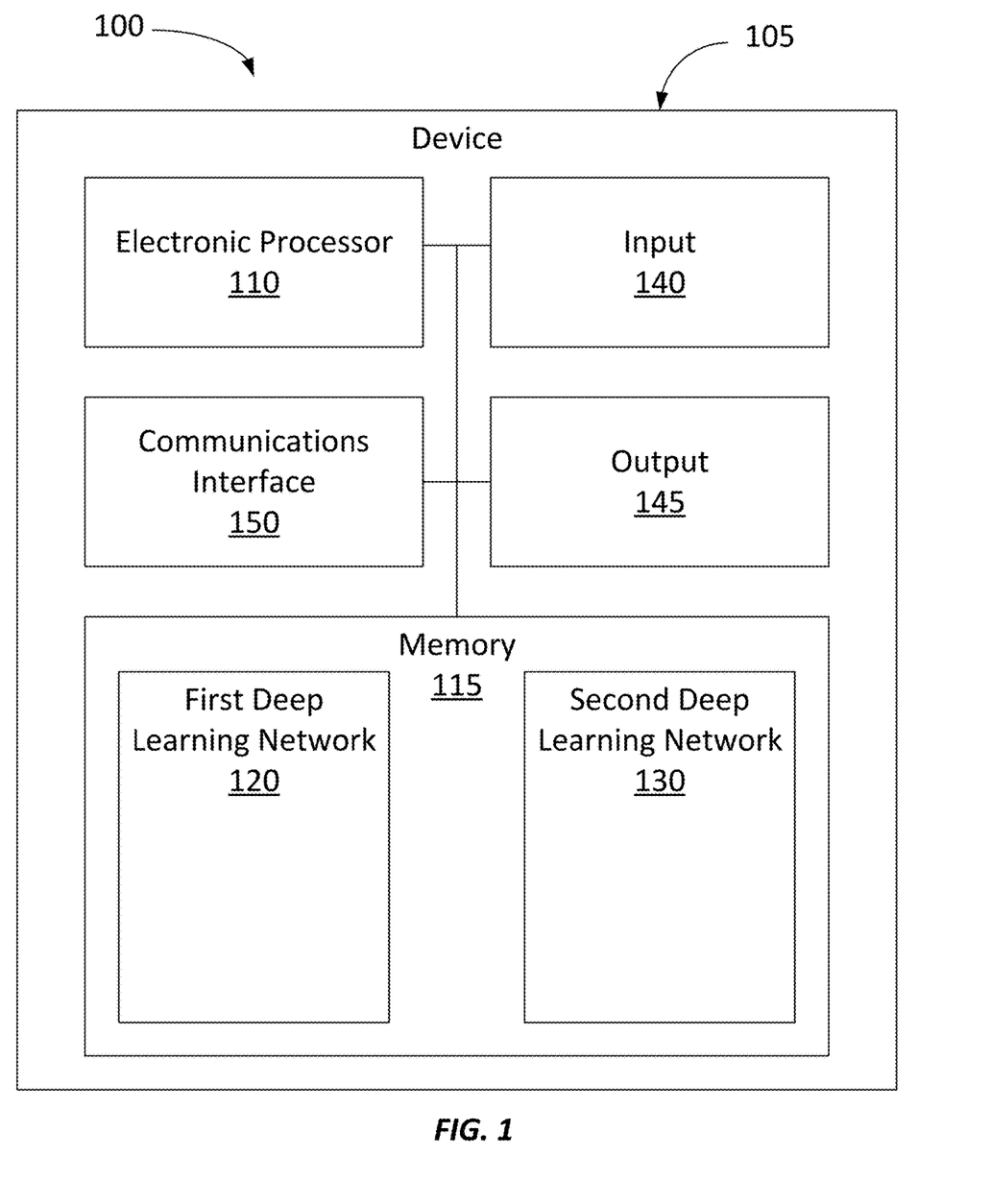
FIG. 1 schematically illustrates a computer-aided diagnosis (CAD) system according to some embodiments.

FIG. 1 illustrates a computer-aided diagnosis (CAD) system 100 according to some embodiments of the invention. The CAD system 100 includes a computing device 105. The computing device 105 may be a server, a personal computer, a tablet computer, or the like. The computing device 105 includes a plurality of electrical and electronic components that provide power, operational control, and protection of the components within the computing device 105. For example, as illustrated in FIG. 1, the computing device 105 includes an electronic processor 110 (a microprocessor, application-specific integrated circuit (ASIC), or another suitable electronic device), a memory 115 (a non-transitory, computer-readable storage medium), and a communications interface 150. The electronic processor 110, the memory 115, and the communications interface 150 communicate over one or more connections or buses. Additionally, as illustrated in FIG. 1, the computing device 105 include an input 140 and an output 145. According to some embodiments, the input 140 and output 145 may be connected directly to the device 105. According to other embodiments, the input 140 and output 145 may be connected via a wireless communication network. The input 140 can include one or more devices for receiving input, such as from a user (e.g. a keyboard, a mouse, a joystick, a microphone, etc.). Similarly, the output 145 can include one or more devices for providing output, such as to a user (e.g., a display device, a speaker, a LED, a printer, etc.). In some embodiments, the computing device 105 includes a single device that provides functionality of both an input 140 and an output 145, such as, for example, a touchscreen. It should be understood that the device 105 illustrated in FIG. 1 represents one example of a device and embodiments described herein may include a device with additional, fewer, or different components than the device 105 illustrated in FIG. 1. Also, in some embodiments, the device 105 performs functionality in addition to the functionality described herein. Similarly, the functionality performed by the device 105 (through execution of instructions by the electronic processor 110) may be distributed among multiple devices (for example, multiple servers in a cloud-based computing system). Accordingly, functionality described herein as being performed by the electronic processor 110 may be performed by one or more electronic processors included in the device 105, external to the device 105, or a combination thereof.

The memory 115 may include read-only memory (ROM), random access memory (RAM) (for example, dynamic RAM (DRAM), synchronous DRAM (SDRAM), and the like), electrically erasable programmable read-only memory (EEPROM), flash memory, a hard disk, a secure digital (SD) card, other suitable memory devices, or a combination thereof. The electronic processor 110 executes computer-readable instructions ("software") stored in the memory 115. The software may include firmware, one or more applications, program data, filters, rules, one or more program modules, and other executable instructions. For example, the software may include instructions and associated data for performing the methods described herein. For example, as illustrated in FIG. 1, the memory 115 may store a first deep learning network 120 and a second deep learning network 130 for performing condition diagnosis as described herein. As also described in more detail below, in some embodiments, the first deep learning network 120 may include one or more convolution layers, and the second deep learning network 130 may include a plurality of convolution layers and one or more convolutional long short-term memory (LSTM) layers. In some embodiments, the LSTM layers are unidirectional LSTM layers. In other embodiments, the LSTM layers are bidirectional LSTM layers. It should be understood that the functionality described herein as being performed by the first deep learning network 120 and the second deep learning network 130 may be distributed among multiple software modules, hardware components, or a combination thereof stored or included in the computing device 105 or external to the computing device 105.

The communications interface 150 allows the computing device 105 to communicate with devices external to the computing device 105. The communications interface 150 may include a port for receiving a wired connection to an external device (for example, a universal serial bus (USB) cable and the like), a transceiver for establishing a wireless connection to an external device (for example, over one or more communication networks, such as the Internet, a local area network (LAN), a wide area network (WAN), and the like), or a combination thereof. In some embodiments, the communications interface 150 allows the computing device 105 to access one or more image repositories storing a plurality of medical images. As described in more detail below, the medical images stored in these image repositories may be used to train the networks described herein, test the networks described herein, be processed by the networks described herein to provide a diagnosis or prediction, a combination thereof. In some embodiments, these images may be stored in the memory 115, in one or more external memories accessible by the computing device 105, or a combination thereof.

As described below, the first deep learning network 120 or the second deep learning network 130 may be "trained" using various machine learning techniques and with various training data. In some embodiments, the first deep learning network 120 or the second deep learning network 130 may be trained using existing image studies with manually specified annotations (e.g., highlighting portions of images including PE). In some embodiments, the first deep learning network 120 or the second deep learning network 130 may include Gradient-weighted Class Activation Mapping (Grad-CAM). In some embodiments, the first deep learning network 120 is one selected from a group consisting of ResNet, DenseNet, and SqueezeNet. In other embodiments, the first deep learning network 120 is one selected from a group consisting of U-Net, V-Net, and Convolutional Autoencoders.

The computing device 105 (or a collection of computing devices as part of a distributed computing environment) is configured to train the first deep learning network 120 and the second deep learning network 130 and, in particular, is configured to perform the training methods described below. In some embodiments, the computing device 105 is also configured to use or apply the networks 120, 130 after training (e.g., to generate a probability of a patient having a condition based on a set of medical images obtained for the patient). However, it should also be understood that, in some embodiments, separate computing devices may be used to train a network and use or apply the network once trained. Also, in some embodiments, a separate computing device may be used for each stage of training as described below.

As noted above, a two-stage training strategy is used to train the CAD system 100. In the first stage (also referred to herein as Stage I), a 2D convolutional network is trained on a limited set of pixel-level annotated image slices. In the second stage (also referred to herein as Stage II), a volumetric computer tomography (CT) image is provided to the CAD system 100. The CT image may include a plurality of slices. For each slice in the CT image, the network from the first stage serves as an image encoder and provides encoded features for the second stage. A recurrent network in the second stage incorporates the features from all the slices and provides diagnosis of a condition.

For example, in the first stage, a classification network (e.g., a 2D convolutional network, also referred to herein as the first deep learning network 120) is trained as an image encoder based on annotated 2-D image slices. To improve the overall performance of the classification network, attention maps are produced, and the produced attention maps are supervised while training the network. In this way, the network prediction is based on the suspicious (e.g., PE) regions on which the network is expected to focus on. This can be achieved by training the first deep learning network 120 with a combination of classification and attention losses.

Attention maps can be used as a retrospective network visualization method. To make the attention trainable, embodiments described herein generate the attention maps during training. Based on the fundamental framework of Grad-CAM, for a given image I, let the last convolutional layer produce K feature maps, $f^k \in R^{u \times v}$. The gradient of the score for class c, $g^c$, is computed with respect to the feature maps $f^k$, and $\partial g^c / \partial f^k$ is obtained. The neuron importance weights $\alpha^c_K$ are obtained by global average-pooling over these gradients flowing back.

$$\alpha^c_K = \frac{1}{u \times v} \sum_i \sum_j \frac{\partial g^c}{\partial f^k_{ij}} \quad (1)$$

These weights capture the importance of feature map k for the target class c. The weighted combination of the activation maps is then calculated, followed by a ReLU operation to obtain the attention map $A^c$ for class c:

$$A^c = ReLU\left(\sum_K \alpha^c_K f^K\right) \quad (2)$$

In some embodiments, the ReLU operation is applied to only include the features that have a positive influence on the class of interest. However, it should be understood that other operations may be used. The attention map can be normalized by its maximum value to range between 0 and 1 when the attention map contains non-zero values. For negative samples, the attention maps are most likely to be all zeroes, and normalization may not be performed. In some embodiments, the spatial resolution of the attention map is the same as the final convolutional layer. According to some embodiments described herein, ResNet18 (i.e., a residual neural network that is 18 layers deep) is used as the classification network (i.e., the first deep learning network), thus the attention map contains 24×24 pixels for an input image of size 384×384. The pixel-level PE segmentation masks may be down-sampled by the same factor to match the size of the attention maps. Bi-linear interpolation may be used for down-sampling, wherein the resulting low-resolution mask includes a blurred version of the original mask and contains floating numbers between 0 and 1. A binary map from the low-resolution masks may be produced by setting any values larger than 0 to 1. It should be understood that producing a mask as described above can result in slightly larger PE masks than actual image sizes. However, the task here is supervising the attention instead of training a segmentation network. Accordingly, as long as the masks cover the PE lesions, they do not necessarily have to be exact. In some embodiments, the attention map may be a different resolution and contain more or less pixels. Accordingly, the input image may be a different resolution and contain more or less pixels based on the number of pixels of the attention map.

In some embodiments, such as within the context of PE, there are two classes: PE-positive and PE-negative. Let y be the ground-truth PE classification label and $\hat{y}$ the network PE prediction score; A be the attention map corresponding to the positive class and M be the down-sampled PE segmentation mask. A loss function used to update the network parameters is defined as:

$$L_{total}=L_{CE}(\hat{y},y)+\lambda L_{CDC}(A,M) \quad (3)$$

where the classification loss, $L_{CE}$, is the categorical cross-entropy loss, and the attention loss, $L_{CDC}$, is the continuous dice coefficient. $\lambda$ is the weighting parameter depending how much emphasis is placed on the attention supervision. For the negative samples, an all-zero mask with the same size may be used. Medical images provided may be slab-based input images (5 slices/slab in this study) to better utilize the neighboring spatial information, where only the central slice in a slab has the corresponding annotation mask. In some embodiments, more or less slices are included in a slab. For example, some embodiments may include 3 slices per slab, while others may include 7 slices per slab.

Figure 2:
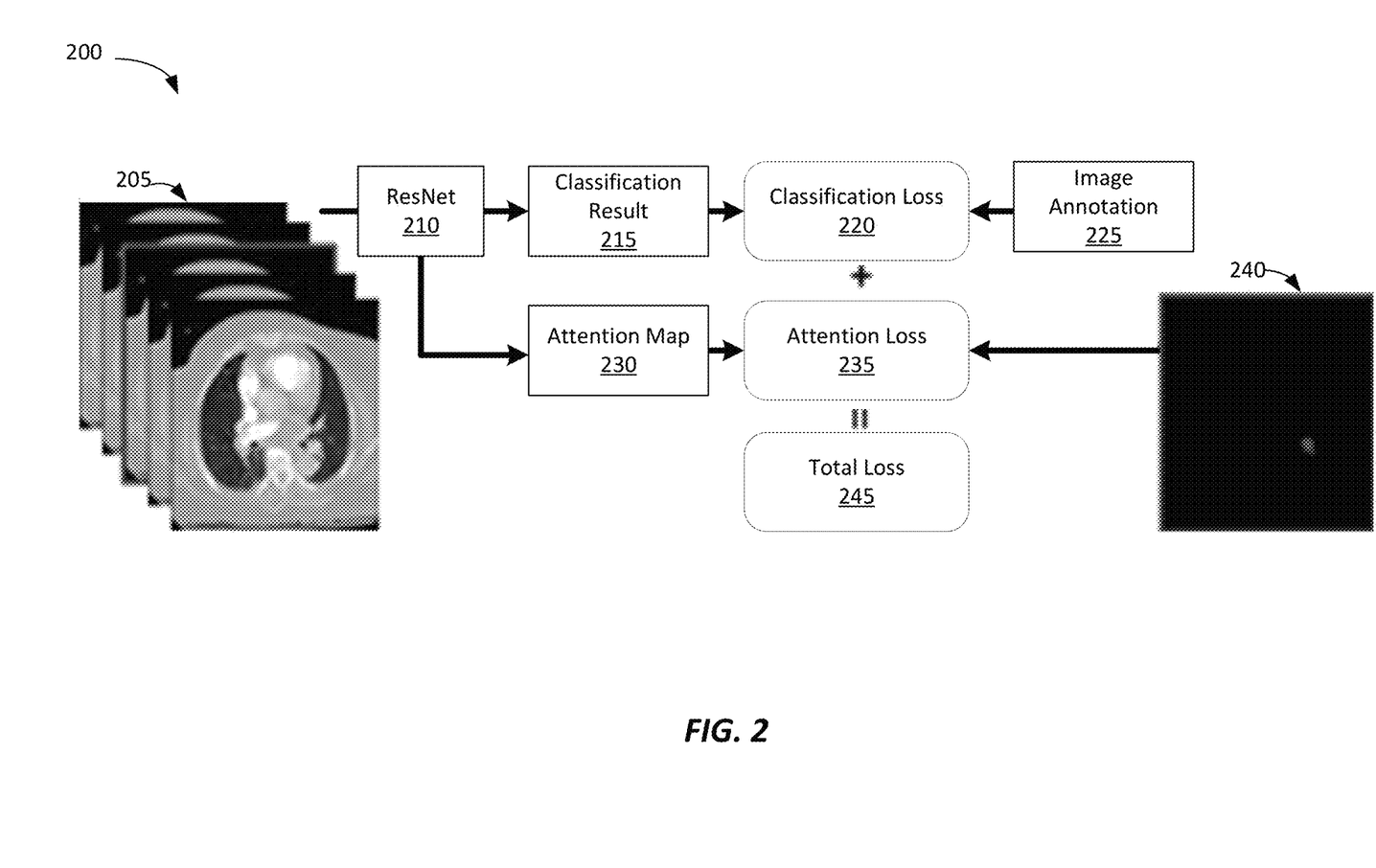
FIG. 2 is a diagram illustrating a first stage of training the CAD system of FIG. 1 according to some embodiments.

For example, FIG. 2 is a diagram 200 illustrating the first stage of training described above according to some embodiments. As illustrated in FIG. 2, a 2D slab image 205 is input to the CAD system 100. A ResNet18 210 may be applied to generate a classification result 215 and an attention map 230. The classification result 215 may be compared against an image annotation 225 to determine a classification loss 220. The attention map 230 may be compared against a PE annotation mask 240 to determine an attention loss 235. The classification loss 220 and the attention loss 235 may be combined to determine a total loss 245.

During the second stage, the ResNet18 210 can a provide PE inference on each 2D image slice of the 2D slab image 205. To obtain a patient-level PE inference, the results from different slices may be integrated. Slice-level predictions may be summarized (e.g., via an average operation or a max operation) into a single patient-level probability. However, this approach may fail to account for spatial context between the slices in a volumetric image. For example, isolated positive samples throughout a volume are more likely to represent false positives due to noise, while a series of consecutive positive slices may indicate a positive PE on the patient level.

Recurrent neural networks such as convolutional long-short term memory (Cony-LSTM) are capable of interpreting and summarizing patterns among correlated samples. For example, bidirectional Conv-LSTM units can be used to scan through a series of consecutive slices from an image volume to detect a condition. Accordingly, as described in more detail below, during the second stage of training a recurrent neural network can be used.

Figure 3:
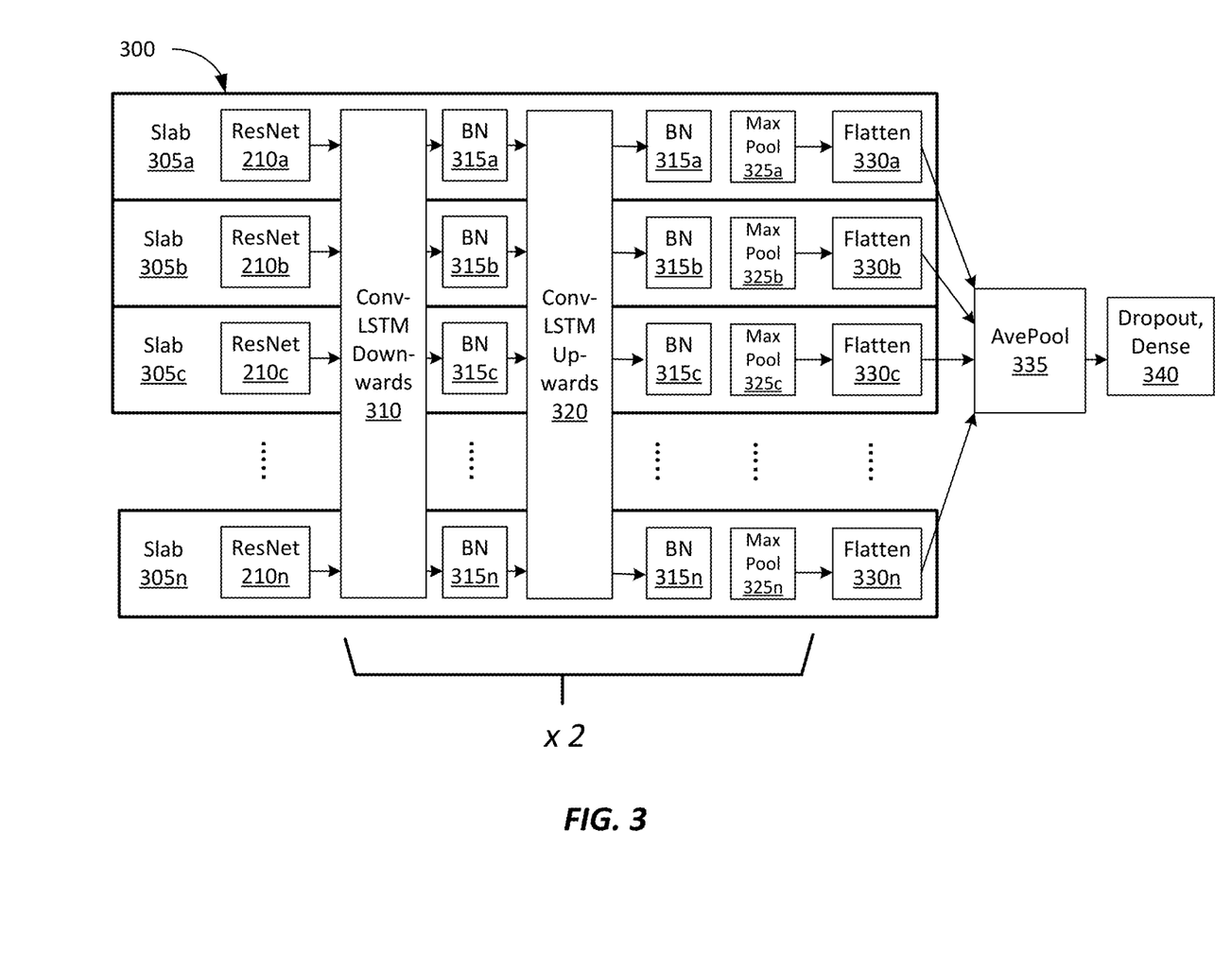
FIG. 3 is a diagram illustrating a second stage of training the CAD system of FIG. 1 according to some embodiments.

For example, FIG. 3 is a diagram 300 illustrating the second stage of training according to some embodiments. During the second stage of training, the pre-trained ResNet18 from the first stage of training is applied to each slab in a volumetric image. In some embodiments, instead of using the classification or attention of the ResNet18 as the input to the recurrent network, the last convolution layer after activation is used to preserve the complete information embedded in the feature map. For example, as illustrated in FIG. 3, image slabs 305a-n, wherein n represents a last image slab in a volumetric image, are each analyzed by the ResNet18 (i.e., ResNet18 210a-n). In other embodiments, instead of using the classification or attention of the ResNet18 as the input to the recurrent network, the last convolution layer before activation is used. In still other embodiments, other convolution layers (not necessarily the last layer before or after activation) is used.

As also illustrated in FIG. 3, in one embodiment, the recurrent framework (i.e., the second deep learning network 130) used during the second stage of training includes two units. Each unit consists of one or more descending Conv-LSTM units 310 and/or one or more ascending Conv-LSTM units 320, followed by a max-pooling layer 325a-n with a pooling size of 2×2 and stride of 2. A batch normalization step 315a-n is applied after each Conv-LSTM layer 310, 320. Each Conv-LSTM layer 310, 320 has 96 filters with a 3×3 kernel size. A channel-wise dropout step 330a-n of rate 0.2 is also applied to the inputs and the recurrent states in the Conv-LSTM layers 310, 320. The final Conv-LSTM layer 320 outputs a series of features that summarize the network findings after processing through the image volume. After an average pooling layer 335 integrates the features along the z-axis, a fully connected layer 340 with sigmoid activation and dropout with a rate of 0.5 computes a probability of the presence of PE. In some embodiments, such as the embodiment illustrated in FIG. 3, two descending Cony-LSTM units 310 and two ascending Conv-LSTM units 320 are used. In other embodiments, more or less of each of the Conv-LSTM units 310, 320 may be used. In some embodiments, the Conv-LSTM units 310, 320 may be in a different order (e.g., ascending Conv-LSTM unit 320 used before descending Conv-LSTM unit 310). In some embodiments, binary cross entropy (BCE) loss is used to update the network.

In some embodiments, the second deep learning network 130 has the flexibility to use either a unidirectional LSTM network or a bidirectional LSTM network. Also, in some embodiments, the second deep learning network 130 (also referred to herein as the feature extractor) is implemented as a neural network that dispenses recurrence completely. Typically, when using an LSTM, each slice within a volume is processed sequentially where the input to the next cell of the LSTM is dependent on the hidden representation from the previous cell. Instead of this configuration, the LSTM network used to implement the second deep learning network 130 can be configured such that features for each slice are extracted parallelly using an attention based neural-network architecture known as a Transformer. A Transformer allows computation of correlations by defining Query, Key, and Value vectors to represent input data. Using a scalar dot product function (described above) as the attention function, the Query and Key vectors are transformed and a softmax function can further be applied to the transformed Query and Key vectors to generate attention weights. Accordingly, in this configuration, the features corresponding to each slice can be provided as a weight representation of the Value vectors, which are obtained by multiplying the attention weights with the Value vectors.

Figure 4:
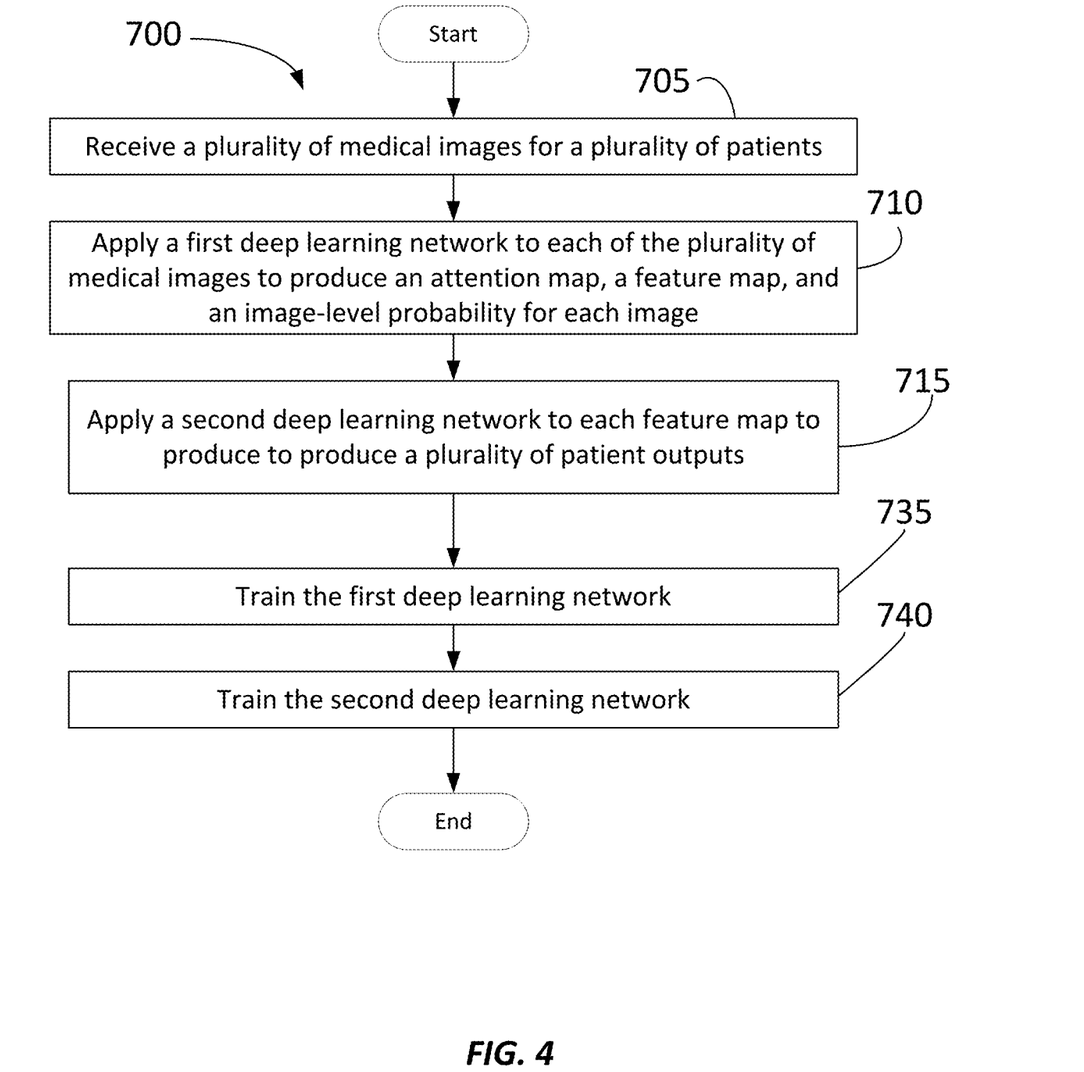
FIG. 4 is a flowchart illustrating a method of training the CAD system of FIG. 1 according to some embodiments.
Figure 5:
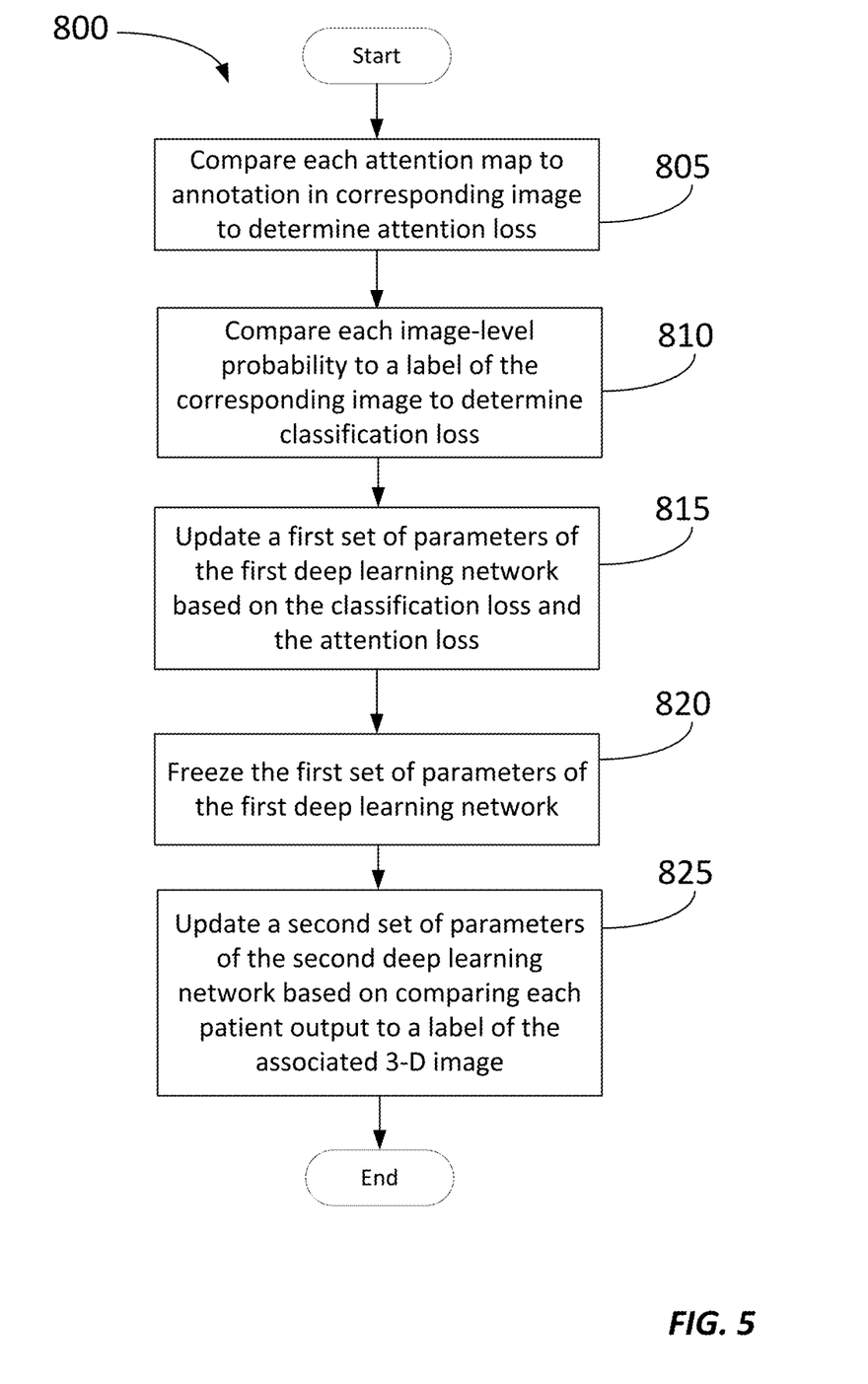
FIG. 5 is a flowchart illustrating a method of training a first deep learning network and a second deep learning network of the CAD system of FIG. 1 as part of the method of FIG. 4 according to some embodiments.

It should be understood that the two-stage training described above can be implemented in various ways. For example, in some embodiments, the attention training associated with the first deep learning network 120 is performed using the attention map produced by the first deep learning network 120. In other embodiments, however, the first deep learning network 120 produces a segmentation map (e.g., a disease lesion segmentation map), which is used to perform the attention training. Also, in some embodiments, the first deep learning network 120 is trained during the first stage of training and its parameters are frozen during the second stage of training. However, in other embodiments, the first deep learning network 120 is trained during the first stage of training but additional training (e.g., updating of parameters) of the first deep learning network 120 is performed as part of the second stage of training. Also, different pooling options exist for processing outputs associated with individual slices to obtain a patient-level output (e.g., a probability that a patient has a condition). FIGS. 4 through 5 described below provide further details regarding these various implementation options.

For example, FIG. 4 illustrates a method 700 for training the CAD system 100 according to some embodiments. The method 700 includes receiving a plurality of medical images for a plurality of patients (at block 705). The medical images may be a plurality of two-dimensional (2-D) images wherein subsets of these images may represent a three-dimensional (3D) image (also referred to as a slab). In other words, a plurality of 3-D medical images can be received, wherein each 3-D medical image includes a plurality of 2-D images (also referred to as slices). At least a portion of the received 2-D images include an annotation (i.e., at least one pixel-level annotation) associated with the condition (e.g., indicating evidence of the condition within the image). In some embodiments, the received medical images also includes some 2-D images (included as part of a 3-D slab) that do not include any annotations associated with the condition. In some embodiments, these 2-D images may only be used during the second stage of training. Also, each of the 3-D slabs represented by the received 2-D images may be associated with a label indicating, at a patient level, whether the patient has the condition (e.g., has pulmonary embolism or not). Accordingly, while in some embodiments, only a portion of the received images include annotations at a pixel-level, all of the received images are associated with a patient-level label indicating presence of the condition (e.g., via a corresponding 3-D slab that is associated with a label indicating PE positive or PE negative).

As illustrated in FIG. 4, the method 700 also includes iteratively applying the first deep learning network 120 to each of the plurality of received medical images to produce an attention map, a feature map, and an image-level probability for each of the plurality of medical images (e.g., each of the plurality of 2-D images) (at block 705). In some embodiments, the attention map is calculated based on Gradient-weighted Class Activation Mapping (GradCAM). Also, as noted above, in some embodiments, the first deep learning network 120 includes any type of convolutional network that can be used for image classification, such as, for example, ResNet, DenseNet, SqueezeNet, or similar networks). These networks generally include one or more convolutional layers followed by a global average pooling layer and one or more dense layers. With this type of network structure, the image-level probability can be the output of the one or more dense layers and the feature map can be the output of a last convolutional layer before the global average pooling layer. As illustrated in FIG. 4, the method 700 also includes applying the second deep learning network 130 to each feature map produced by the first deep learning network to produce a plurality of patient outputs (at block 715). For example, for each feature map produced via the first deep learning network 120, the CAD system 100 applies the second deep learning network 130 to the feature map to generate an output. Since a feature map is produced by the first deep learning network 120 for each received image (i.e., each received 2-D image) and an output is produced by the second deep learning network 130 for each feature map, a plurality of outputs are produced by the second deep learning network 130, wherein each output is associated with one of the plurality of 2-D images. The outputs are used to produce the patient outputs, which may include a patient-level probability of the condition. For example, in some embodiments, the patient-level probability is a probability of the patient associated with a series of 2-D images representing a particular 3-D slab has the condition (e.g., a PE). In some embodiments, the second deep learning network 130 produces the patient outputs by pooling or aggregating outputs produced by the second deep learning network 130 for each feature map associated with a series of 2-D images representing a 3-D image for a particular patient. These outputs can be aggregated by an aggregation function selected from a group consisting of a mean function, a max function, a mode function, and a self-attention function. In some embodiments, the self-attention function can be used as an aggregator function and can be implemented as a scalar dot product attention. For example, the self-attention function can include a third deep learning network comprised of, for example, two fully connected dense layers and two non-linear activation function layers. Parameters of the self-attention function can be trained along with the second deep learning network 130 as described above. In other embodiments, the self-attention function can include a multi-head attention function, which can be designed as a neural network including two fully connected dense layers and two non-linear activation layers. When using the multi-head attention function multiple sets of attention weight parameters can be learned (as opposed to learning only a single set of attention weight parameters) to capture more generalizable weights. The multi-head attention weights can be combined through concatenation or by taking a sum or an average across each set of weights. It should be understood that when a self-attention network is used as an aggregator function, the network can be interpretable in nature and helps select image slices (i.e., 2-D images) that have the most salient and discriminative information to contribute to the volume-level feature. The self-attention network thus saves time and processing resources as only key slices (e.g., CT slices) are processed for specific downstream tasks that otherwise is bottlenecked by having to process all slices of a volume (e.g., a CT volume).

As illustrated in FIG. 4, the method 700 also includes training the first deep learning network 120 (at block 735) and training the second deep learning network 130 (at block 740). As described in more detail above and below, in some embodiments, the first deep learning network 120 is trained using back propagation to reduce a loss function, wherein the loss function can include a classification loss function, an attention loss function, or a combination thereof. As for the second deep learning network 130, this network 130 can be trained to minimize a classification loss, such as by using a binary cross-entropy loss or a focal local as the objective function. In some embodiments, using focal loss allows the CAD system 100 to better handle data imbalance, since using focal loss penalizes easy samples (e.g. large number of condition negatives) and forces the system 100 to learn more robust representations about the hard samples (e.g., condition positives).

FIG. 5 illustrates a method 800 for training the first deep learning network 120 and the second deep learning network 130 (e.g., as part of blocks 735 and 740 of method 700) according to some embodiments. The method 800 includes comparing an attention map produced by the first deep learning network 120 (at block 710) to an annotation in a corresponding image to produce an attention loss (at block 805). As noted above, a portion of the received medical images (i.e., 2-D images include a pixel-level annotation associated with the condition). Accordingly, in this part of the training, the annotation of each of these images can be compared the associated attention map produced by the first deep learning network 120 to determine the attention loss. In some embodiments, determining the attention loss includes comparing the attention map with a down-sampled version of the corresponding 2-D image. Alternatively, in other embodiments, the determining the attention loss includes comparing an up-sampled version of the attention map with the corresponding 2-D image.

The method 800 also includes comparing each image-level probability produced by the first deep learning network 120 with a label of the corresponding medical image (e.g., the label of the associated 3-D slab) to determine a classification loss (at block 810). The attention loss and the classification loss are then used to update a set of parameters of the first deep learning network 120 (at block 815).

As illustrated in FIG. 5, in some embodiments, the method 800 also includes freezing the parameters on the first deep learning network 120 (e.g., before training the second deep learning network 130) (at block 820). In particular, after freezing the first set of parameters (at block 820), the method 800 can include updating a second set of parameters of the second deep learning network 130 based on comparing the patient output produced by the second deep learning network 130 (at block 715) to the label of the corresponding medical images associated with the patient output (e.g., the label for the corresponding 3-D slab of a patent) (block 825). It should be understood that, in some embodiments, the first set of parameters updated during training of the first deep learning network 120 (at block 815) are not frozen during training of the second deep learning network 130. Accordingly, in this implementation, the first set of the parameters and the second set of a parameters can be updated based on the comparison of patient output (i.e., patient probability) with the associated label.

In some embodiments, rather than producing an attention map via the first deep learning network 120, the first deep learning network 120 produces a segmentation map, such as a disease lesion segmentation map. In these embodiments, the segmentation maps are used during the training of the first deep learning network 120 in place of the attention maps and, thus, this part of the training determines a segmentation loss as compared to an attention loss. In this implementation, the first deep learning network 120 can include any type of convolutional network that can be used for image segmentation, such as, for example, U-Net, V-Net, Convolutional Autoencoders, and other similar networks. These types of networks generally include one or more encoding convolutional layers, one or more bottleneck convolutional layers, and one or more decoding convolutional layers. One or more dense layers can also be attached to a last bottleneck convolutional layer, and the image-level probability produced by the first deep learning network 120 in such construction can be an output of the one or more dense layers. Similarly, the feature map can be the output of a last of the one or more bottleneck convolutional layers and the segmentation map can be the output of a last of the one or more decoding convolutional layers.

In either the attention map or the segmentation map implementation, the input provided to the second deep learning network 130 can be flexibly chosen to either represent instance features obtained on the slice level or masked 3-D images obtained on the volume level. The masked images can be obtained by combining raw volumetric data with the lesion segmentation map or attention map from the first deep learning network 120. In some embodiments, the operation used to create a masked image is the Hadamard product applied between the pixels of both the raw image and the map.

A specific implementation of the systems and methods described herein will now be described with respect to test data, which demonstrates the technical improvements provided via the two-stage training described above. For the particular test described herein, test data came from various hospitals and were acquired from various makes and models of CT scanners. All studies were contrast-enhanced but were not limited to PE protocol studies. For training and validation, 5,856 studies marked as positive by an NLP algorithm used by the data provider were used. A large cohort of contrast-enhanced CT study and radiology report pairs from the data providers without any labels were also used. From this cohort, 5,196 studies were selected as PE negatives by an NLP algorithm. Furthermore, a subset of positive and negative studies were more rigorously verified for training and validation in Stage I. 1,670 positive studies were manually annotated by board-certified radiologists. For each annotation, a radiologist segmented every embolism in slices approximately 10 mm apart. This annotation process leaves several un-annotated slices between two annotated slices. A total of 10,388 slices were annotated.

Additionally, another 2,160 independent studies (517 positive and 1,643 negatives) were selected as a test set. Radiology reports of the studies in the test set were manually reviewed to confirm the label.

To train the network in Stage I, image slabs produced from 10,388 annotated slices were used as positive samples and an equal number of randomly selected slabs from 593 negative studies were used as negative samples. These studies had various slice thicknesses ranging from 0.5 mm to 5 mm, with a median of 2 mm. As variances in slice thickness could cause instability when training the network using slab-based data, the volumetric images were resampled to have a 2.5 mm slice thickness using bilinear interpolation. Then, image slabs of 5 slices were selected around the annotated slices. All the image slabs were cropped to size 384×384 around the center, and the values between −1024 HU and 500 HU were mapped to 0-255.

Labeled volumetric images were used for training of Stage II and for testing. For Stage II training, in addition to the studies used in Stage I, an additional 4,186 positive and 4,603 negative studies were included, which resulted in a total of 5,856 positive and 5,196 negative volumetric images. The image slices containing a lung were identified using a lung segmentation tool. Those slices were resized to 200 slices and then sampled every 4 slices to obtain 50 slabs where each slab contains 5 slices. After image cropping and value mapping (same as in Stage I), the input image size of each study was 50×384×384×5. For each study, the input to the network in Stage II is the output of last convolutional layer of the trained ResNet18 in Stage I, which is a tensor of size 50×24×24×512. During the training of the Stage II network, the weights of the Stage I network were fixed and not updated.

The framework was implemented using Keras and trained on two NVIDIA Tesla P100 GPUs. The ResNet18 in Stage I was trained for 100 epochs with a batch size of 48 and the model with the highest validation accuracy was selected and used in Stage II. The recurrent network in Stage II was trained for 50 epochs with a batch size of 32 and the model with the highest validation accuracy was finally selected. For both stages, 80% of the data was used for training and the remaining 20% for validation. An Adam optimizer with a learning rate of 10-4 was used.

Figure 6:
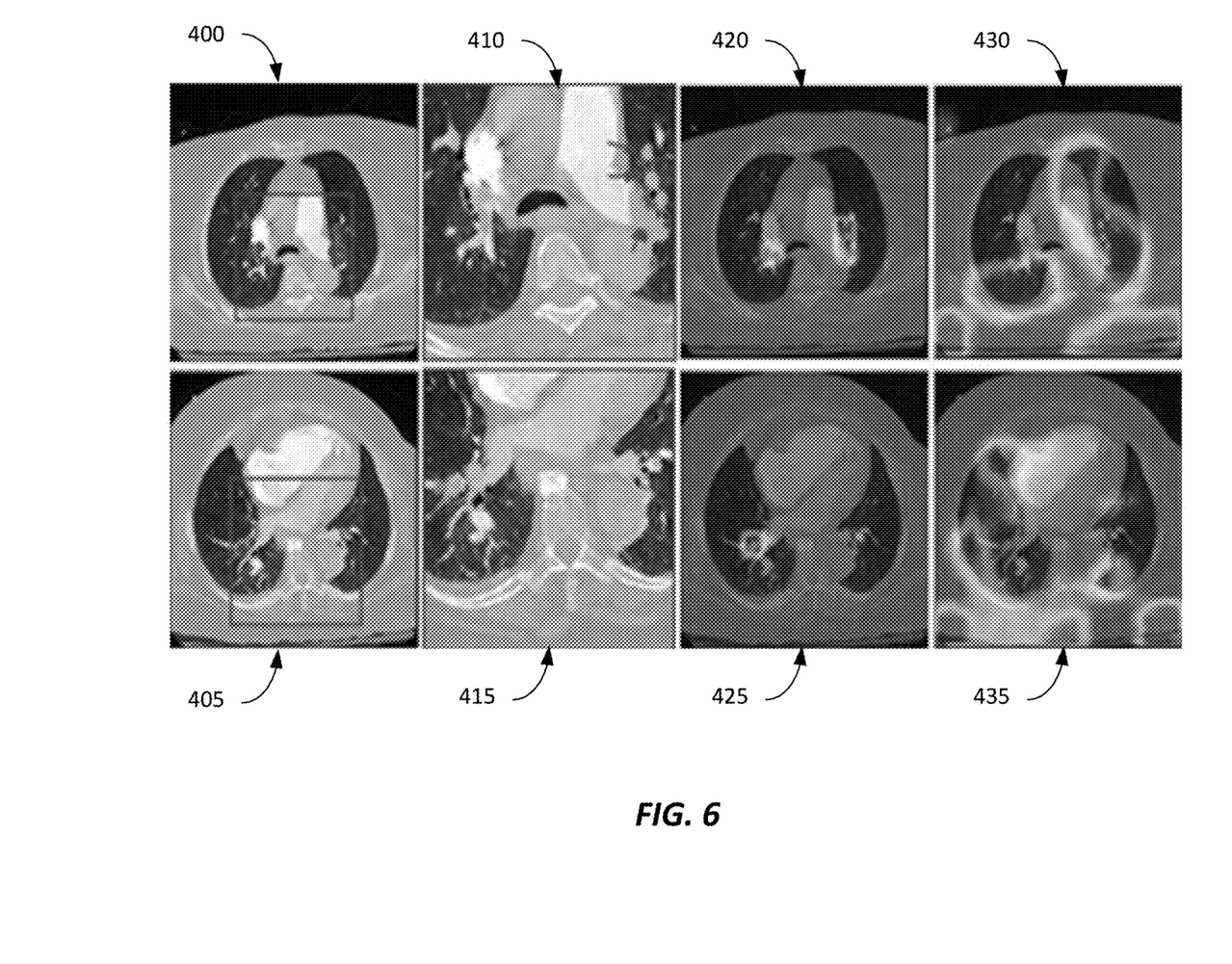
FIG. 6 is a first set of attention maps generated by the system of FIG. 1 according to some embodiments.

FIG. 6 is a first set of attention maps generated by the CAD system 100. The first set of attention maps were generated from an image slab in a test data set with and without attention training in Stage I. Images 400 and 405 are annotated medical images (i.e., by a radiologist) with a box around the area in which PE may be located. Images 410 and 415 are enlarged versions of the boxed regions of images 400 and 405, including annotations directing to the potential PE. Images 420 and 425 are attention maps generated by a system trained according to Stage I. The attention maps in images 420 and 250 are localized and show strong concordance with the annotation masks produced by the radiologist shown in images 400 and 405. Images 430 and 435 are attention maps generated by a system not trained according to stage I. The attention maps in images 430 and 435 are widely distributed and mostly focused on irrelevant regions where no PE is present.

Figure 7:
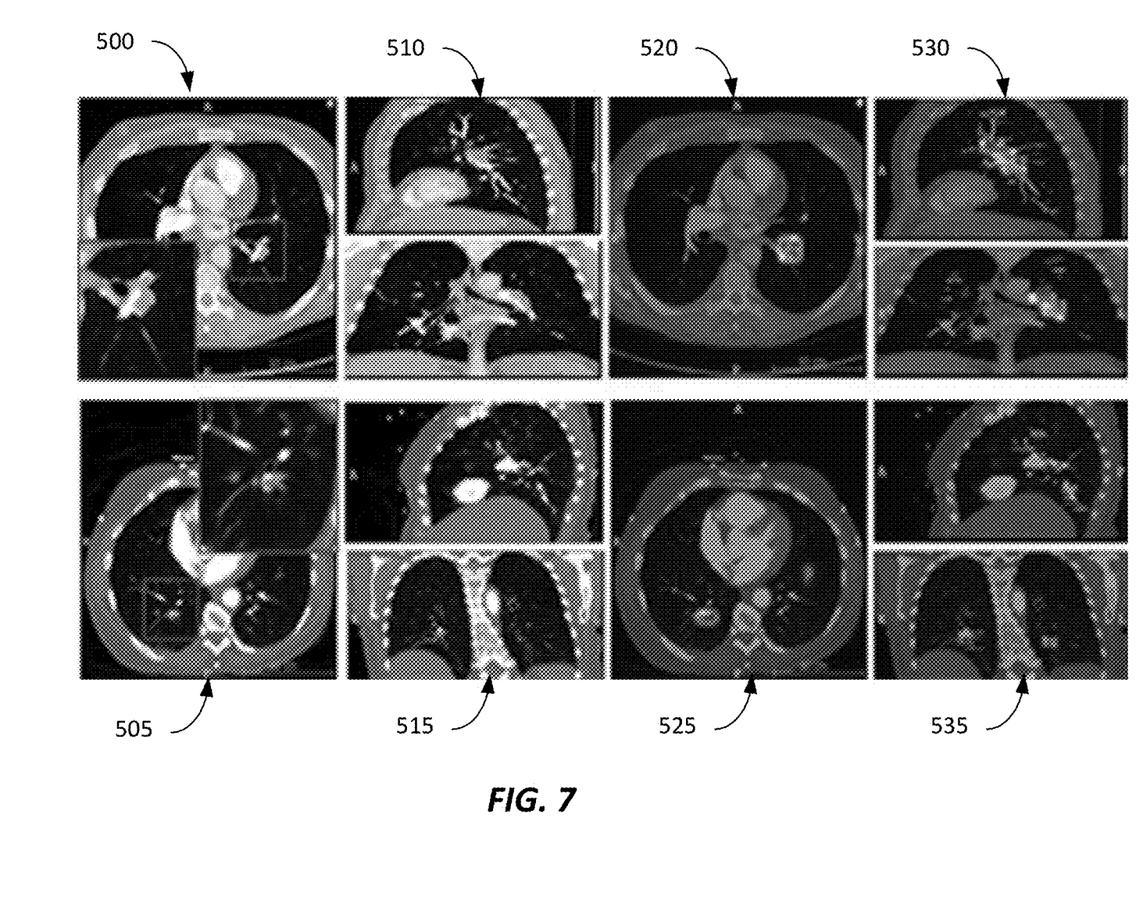
FIG. 7 is a second set of attention maps generated by the system of FIG. 1 according to some embodiments.

FIG. 7 is a second set of attention maps generated by the CAD system 100. Images 500 and 505 are medical images with an enlarged portion containing PE. Images 510 and 515 are medical images including PE. Images 520 and 525 are attention maps highlighting potential PE in the medical images of images 500 and 505, respectively. Images 530 and 535 are attention maps highlighting potential PE in the medical images of images 510 and 515, respectively.

The performance of the system 100 in patient-level prediction of PE was measured on a test set with 2,160 studies in three scenarios. In all these scenarios, the first stage network was trained using 1,670 annotated positive studies and 593 negative studies. Also, the first stage network was frozen during the training of the second stage. In the first scenario, only the data that was used to train the first stage was used to train the second stage (no label-only studies were used). The first stage was trained with a combination of classification and attention losses as in equation (3). In the second and third scenarios, in addition to the data that was used in the first scenario, an additional 8,789 label-only studies were used to train Stage II. The difference between the second and third scenarios is in the loss function that was used to train Stage I. In the second scenario, the Stage I network was trained using classification loss only. In the third scenario, similar to the first scenario, a combination of attention and classification loss was used.

Figure 8A:
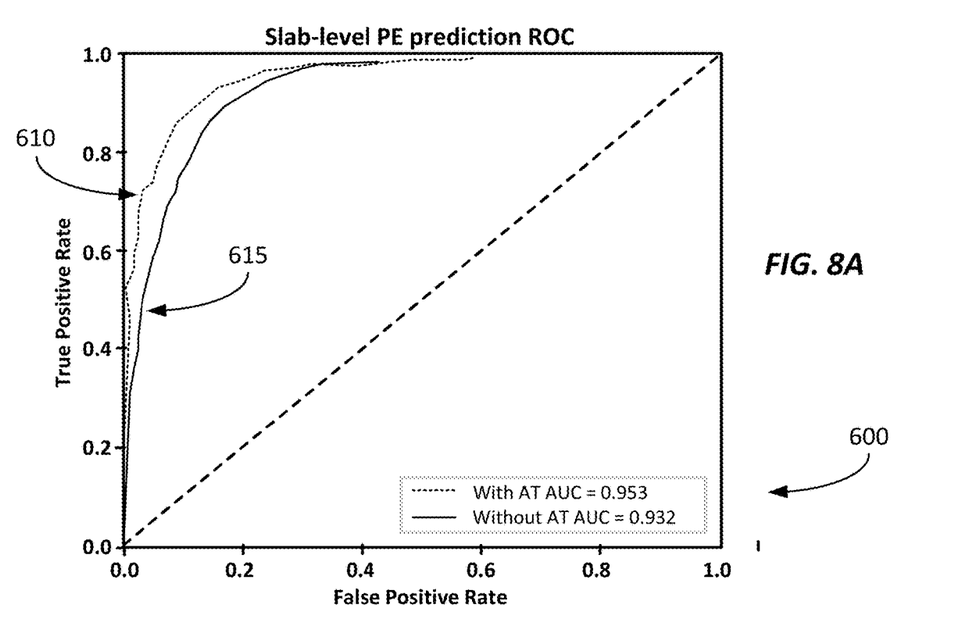
FIG. 8A is a graph illustrating a receiver operating characteristic (ROC) curve of a slab-level PE prediction by the system of FIG. 1 according to some embodiments.

FIG. 8A is a graph 600 illustrating a receiver operating characteristic (ROC) curve of a slab-level PE prediction by the CAD system 100. The graph 600 shows the ROC for the test data following Stage I. As can be seen, using the attention loss significantly improved Stage I's performance by increasing the area under the curve (AUC) from 0.932 (solid curve 615) to 0.953 (dotted curve 610) when trained on the same data. The low performance of the pipeline without attention loss shows that a network with distracted attention that focuses on the correlated background features might still obtain high accuracy in 2D image classification but will not be able to generalize well on patient-level classification based on the inconsistent feature patterns.

Figure 8B:
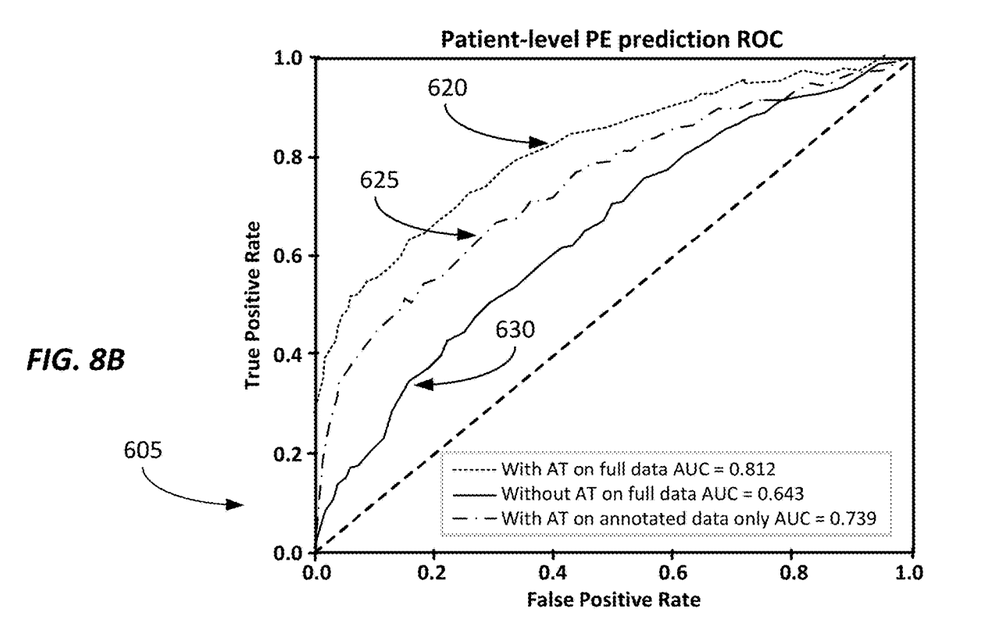
FIG. 8B is a graph illustrating a receiver operating characteristic (ROC) curve of a patient-level PE prediction by the system of FIG. 1 according to some embodiments.

FIG. 8B is a graph 605 illustrating a ROC curve of a patient-level PE prediction by the CAD system 100. The graph 605 shows the ROC of the pipeline for the three test scenarios. As can be seen, using the attention loss significantly improved the pipeline performance by increasing the area under the curve (AUC) from 0.643 (solid curve 630) to 0.812 (dotted curve 620) when trained on the same data. This implies that the ResNet18 in Stage I obtained better PE feature extraction ability with attention training, since the output of the ResNet18's last convolutional layer was used as the input in the recurrent network in Stage II. Neither the classification results nor the attention maps were used. The graph 605 also demonstrates that the pipeline can use a large amount of easily obtainable label-only data samples to increase its accuracy. The AUC increased from 0.739 (dashed curve 625) to 0.812 (dotted curve 620) when 8,789 label-only studies were added to the training data. This is important for scalability of a pipeline to be trained on a large data set. Relying solely on fine annotated data sets for training is not feasible when a large data set is required.

Compared to the state-of-the-art PENet, which achieved an AUC of 0.79 and accuracy of 0.74 on an internal test set, and AUC of 0.77 and accuracy of 0.67 on an external test set, methods according to embodiments described herein obtained an AUC of 0.812 with confidence interval [0.789, 0.835] and accuracy of 0.781 (threshold of 0.5 was used for both PENet and methods according to embodiments described herein) on a much larger test set (2160 versus approx. 200). Moreover, the studies they used were acquired under the same PE protocol at the same institute with a consistent high resolution slice thickness (1.25 mm), whereas test data for testing methods according to embodiments described herein was acquired from various hospitals under different imaging protocols so the images had different noise levels and slice thickness (0.5 mm-5 mm).

A proposed model according to embodiments described herein was also compared with a 3D CNN model that has demonstrated success in acute aortic syndrome detection. The model starts with an I3D model (3D CNN pretrained on video action recognition dataset), followed by Conv-LSTM layers and dense layers as the classifier. The model was trained only on patient-level labeled data, and resulted in an AUC of 0.787 and accuracy of 0.727 (with a threshold of 0.5) on our test set, which is still inferior to results generated by the proposed model according to embodiments described herein. A summary of the test results for different methods is shown in Table 1.

TABLE 1

| Approach | Testset Size | AUC | Accuracy |
|---|---|---|---|
| PENet (int.) | 198 | 0.79 | 0.74 |
| PENet (ext.) | 227 | 0.77 | 0.67 |
| 3D CNN | 2160 | 0.787 | 0.727 |
| Proposed | 2160 | 0.812 | 0.781 |

Thus, embodiments described herein provide methods and systems for training a CAD system using a two-stage training process, wherein, once trained, the CAD system can be used to provide a patient-level probability for a condition, such as pulmonary embolism. It should be understood that although embodiments described herein used pulmonary embolism as the condition being detected, the training processes described herein can be used to train CAD systems to detect other medical conditions in various types of medical images. As described above, using attention-guided training of an initial classification network with a small set of annotated images allows the CAD system to focus attention on a desired feature while allowing the second network (e.g., a recurrent network) to be trained using patient-level labels. Accordingly, not only do the methods and systems described here provide accurate predictions regarding a particular medical condition but they do not require extensive image annotations (i.e., pixel level annotations), which, as noted above, can be difficult to collect.

Various features and advantages of the invention are set forth in the following claims.

What is claimed is:

1. A method of training a computer-aided condition detection system, the method comprising:
    receiving a plurality of medical images for a plurality of patients, a portion of the plurality of medical images including an annotation associated with a condition;
    iteratively applying a first deep learning network to each of the plurality of medical images to produce an attention map, a feature map, and an image-level probability of the condition for each of the plurality of medical images;
    iteratively applying a second deep learning network to the feature map produced by the first deep learning network for each of the plurality of medical images to produce a plurality of patient outputs;
    training the first deep learning network based on the attention map produced by the first deep learning network for each image included in the portion of the plurality of medical images; and
    training the second deep learning network based on the patient output produced by the second deep learning network for each of the plurality of patients,
    wherein the second deep learning network includes a plurality of convolution layers and a plurality of convolutional long short-term memory (LSTM) layers, and
    wherein each of the plurality of patient outputs includes a patient-level probability of the condition for one of the plurality of patients.

2. The method of claim 1, wherein the plurality of medical images include a plurality of two-dimensional (2-D) images, each of a plurality of subsets of the plurality of 2-D images constituting a series of images corresponding to a three-dimensional (3-D) image of one of the plurality of patients, wherein each 3-D image is associated with a label indicating whether one of the plurality of patients has the condition.

3. The method of claim 2, wherein training the first deep learning network includes training the first deep learning network using back propagation to reduce a loss function.

4. The method of claim 3, wherein training the first deep learning network includes:
    for each 2-D image included in the portion of the plurality of 2-D medical images including an annotation of the condition:
        comparing the annotation of the condition to the attention map produced by first deep learning network for the 2-D image to determine an attention loss, and
        comparing the image-level probability produced by the first deep learning network for the 2-D image with a label of the 2-D image to produce a classification loss; and
        updating a first set of parameters of the first deep learning network using one or both of the classification loss and the attention loss.

5. The method of claim 4, wherein training the second deep learning network includes:
    freezing the first set of parameters;
    updating a second set of parameters of the second deep learning network based on comparing the patient-level probability of the condition of each of the plurality of patient outputs to the label of one of the plurality of 3-D images.

6. The method of claim 4, wherein training the second deep learning network includes:
    updating the first set of parameters of the first deep learning network and a second set of parameters of the second deep learning network based on comparing the patient-level probability of the condition of each of the plurality of patient outputs to the label of one of the plurality of 3-D images.

7. The method of claim 4, wherein determining the attention loss includes determining the attention loss based on the attention map and a down-sampled version of the corresponding 2-D image with an annotation associated with the condition.

8. The method of claim 4, wherein determining the attention loss includes determining the attention loss based on an up-sampled version of the attention map and the corresponding 2-D image with an annotation associated with the condition.

9. The method of claim 1, wherein the condition is pulmonary embolism.

10. The method of claim 1, wherein the first deep learning network is one selected from a group consisting of ResNet, DenseNet, and SqueezeNet.

11. The method of claim 1, wherein iteratively applying the first deep learning network to produce the attention map includes producing the attention map based on Gradient-weighted Class Activation Mapping (GradCAM).

12. The method of claim 1, wherein the first deep learning includes one or more convolutional layers followed by a global average pooling layer and one or more dense layers, wherein the image-level probability is an output of the one or more dense layers and the feature map is an output of a last of the one or more convolutional layers before the global average pooling layer.

13. The method of claim 1, wherein iteratively applying the second deep learning network to the feature map produced for each of the plurality of medical images to produce the plurality of patient outputs includes pooling, for each of the plurality of patients, outputs produced by the second deep learning network for a subset of the plurality of medical images.

14. The method of claim 13, wherein pooling the outputs for a subset of the plurality of medical images includes pooling the outputs using an aggregation function, wherein the aggregation function is one selected from a group consisting of a mean function, a max function, a mode function, and a self-attention function.

15. The method of claim 14, wherein the aggregation function is the self-attention function, and the self-attention function is a third deep learning network including a plurality of fully connected dense layers and a plurality of non-linear activation function layers.

16. The method of claim 1, wherein each of the plurality of convolutional long short-term memory (LSTM) layers is one selected from a group consisting of a unidirectional LSTM layer and a bidirectional LSTM layer.

17. The method of claim 1, wherein training the second deep learning network includes training the second deep learning network to minimize a classification loss using at least one selected from a group consisting of a binary cross-entropy loss and a focal loss as an objective function.

18. The method of claim 1, wherein the method further comprises, after training the first deep learning network and after training the second deep learning network:
receiving a three-dimensional (3-D) medical image of a patient, the 3-D image including a plurality of two-dimensional (2-D) medical images of the patient;
iteratively applying the first deep learning network to each of the plurality of 2-D medical images of the patient to produce a plurality of feature maps associated with the patient, wherein each of the plurality of feature maps associated with the patient is associated with one of the plurality of 2-D medical images of the patient;
iteratively applying the second deep learning network to each of the plurality of feature maps associated with the patient to produce a plurality of classification outputs associated with the patient;
pooling the plurality of classification outputs associated with the patient to generate a condition probability of the patient, the condition probability of the patient including a probability of the patient having the condition; and
outputting the condition probability of the patient.

19. A system for training a computer-aided condition detection program, the system comprising:
a computing device including an electronic processor configured to:
receive a plurality of medical images for a plurality of patients, a portion of the plurality of medical images including an annotation associated with a condition;
iteratively apply a first deep learning network to each of the plurality of medical images to produce an attention map, a feature map, and an image-level probability of the condition for each of the plurality of medical images;
iteratively apply a second deep learning network to the feature map produced by the first deep learning network for each of the plurality of medical images to produce a plurality of patient outputs;
train the first deep learning network based on the attention map produced by the first deep learning network for each image included in the portion of the plurality of medical images; and
train the second deep learning network based on the patient output produced by the second deep learning network for each of the plurality of patients,
wherein the second deep learning network includes a plurality of convolution layers and a plurality of convolutional long short-term memory (LSTM) layers, and
wherein each of the plurality of patient outputs includes a patient-level probability of the condition for one of the plurality of patients.

20. Non-transitory computer-readable medium including instructions that, when executed by an electronic processor, perform a set of functions, the set of functions comprising:
receiving a plurality of medical images for a plurality of patients, a portion of the plurality of medical images including an annotation associated with a condition;
iteratively applying a first deep learning network to each of the plurality of medical images to produce an attention map, a feature map, and an image-level probability of the condition for each of the plurality of medical images;
iteratively applying a second deep learning network to the feature map produced by the first deep learning network for each of the plurality of medical images to produce a plurality of patient outputs;
training the first deep learning network based on the attention map produced by the first deep learning network for each image included in the portion of the plurality of medical images; and
training the second deep learning network based on the patient output produced by the second deep learning network for each of the plurality of patients,
wherein the second deep learning network includes a plurality of convolution layers and a plurality of convolutional long short-term memory (LSTM) layers, and
wherein each of the plurality of patient outputs includes a patient-level probability of the condition for one of the plurality of patients.

* * * * *